(12) United States Patent
Carson et al.

(10) Patent No.: US 6,576,420 B1
(45) Date of Patent: Jun. 10, 2003

(54) METHOD FOR EARLY DIAGNOSIS OF, AND DETERMINATION OF PROGNOSIS IN, CANCER

(75) Inventors: Dennis A. Carson, Del Mar, CA (US); Mathias Schmid, Bollingen (DE); Carlos J. Carrera, San Diego, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/335,231

(22) Filed: Jun. 17, 1999

Related U.S. Application Data

(60) Provisional application No. 60/090,411, filed on Jun. 23, 1998.

(51) Int. Cl.$^7$ .......................... C12Q 1/68; C12P 19/34; G01N 33/53; C07H 21/04

(52) U.S. Cl. ...................... 435/6; 435/91.2; 435/7.92; 536/23.1; 536/24.1; 536/24.2; 536/24.3; 536/24.33

(58) Field of Search ...................... 435/6, 91.2, 7.92; 536/23.1, 23.2, 24.1, 24.2, 24.3, 24.33

(56) References Cited

U.S. PATENT DOCUMENTS 5,693,474 A * 12/1997 Shay et al. .................... 435/6

OTHER PUBLICATIONS

Kim S. K. et al., "Identification of Three Distinct Tumor sSuppressor Loci on the Short arm of Chromosome 9 in Small Cell Lung Cancer." Cancer Research, (Feb. 1, 1997), vol. 57. No. 3. pp. 400–403.*
Ohta, M. et al., "Deletions Mapping Of Chromosome Region 9p21–p22 Surrounding the CDKN2 Locus in Melanoma." International Journal of Cancer, (Mar. 15, 1996) vol. 65. No. 6. pp. 762–767.*
Lydiatt, W.M. et al., "9p21 Deletion Correlated with Recurrence in Head and Neck Cancer." Head and Neck (Mar. 1998) vol. 20., No. 2. pp. 113–118.*
Lydiatt, W.M. et al., "Molecular Support ofr Field Cancerization in the Head and Neck." Cancer (Apr. 1, 1998) vol. 82., No. 7. pp. 1376–1380.*
Batova et al. Frequent Deletion in the Methylthioadenosine Phosphorylase Gene in T–cell Acute Lymphoblastic Leukemia: Strategies for Enayme targeted therapy (Blood, vol. 88, No. 8, pp. 3083–3090., Oct. 1996.*
Heyman et al. Prognostic Importance of p15 and p16 gene Inactivation in childhood acute lymphoblastic leukemia, Journal of Clinical Oncology, vol. 14, No. 5, pp. 1512–1520, May 1996.*
Apolone, G., et al., [Comments] "Cancer Staging may have Different Meanings, but Functional Status Too," J. of Clin. Epidemiology (1992) Feb; 45(2):184–186.

Buzaid, A., et al., "Critical Analysis of the Current American Joint Committee on Cancer Staging System for Cutaneous Melanoma and Proposal of a New Staging System," J. of Clin. Oncology (1997) Mar.; 15(3):1039–1051.
Curran, W., et al., "Comparison of the Radiation Therapy Oncology Group and American Joint Committee on Cancer Staging Systems Among Patients with Non–Small Cell Lung Cancer Receiving Hyperfractionated Radiation Therapy," Cancer (1991) Aug.; 68(3):509–516.
Fleming, I., et al., "The National Cancer Data Base Report on Recent Hospital Cancer Program Progress toward Complete American Joint Committee on Cancer/TNM Staging," Cancer (1997) Dec.; 80(12):2305–2310.
Fleming, I., et al., "The National Cancer Data Base Report on Completeness of American Joint Committee on Cancer Staging in United States Cancer Facilities," Cancer (1996) Oct.; 78(7):1498–1504.
Ginsberg, R., et al., "Continuing Controversies in Staging NSCLC: An Analysis of the Revised 1997 Staging System," Oncology (1998); 12 (Supp. 2) Issue 1:51–54.
Greenberg, E., et al., "Cancer Staging may have Different Meanings in Academic and Community Hospitals," J. Clin. Epidemiology (1991); 44(6):505–512.
Kreth, F., et al., "Supratentorial World Health Organization Grade 2 Astrocytomas and Oligoastrocytomas," Cancer (1997) Jan; 79(2):370–379.
Ross, Merrick, M.D., "Modifying the Criteria of the American Joint Commission on Cancer Staging System in Melanoma," Current Opinion in Oncology (1998); 10:153–161.
Sallinen, S., et al, "Accumulation of Genetic Changes is Associated with Poor Prognosis in Grade II Astrocytomas," Amer. J. of Pathology (1997) Dec.; 151(6):1799–1807.
Shaw, E., et al., "Supratentorial Gliomas: A Comparative Study by Grade and Histologic Type," J. of Neuro–Oncology (1997); 31:273–278.

* cited by examiner

Primary Examiner—Kenneth R. Horlick
Assistant Examiner—Christine Maupin
(74) Attorney, Agent, or Firm—Townsend and Townsend and Crew LLP

(57) ABSTRACT

The invention provides a method for diagnosis of, and determining a prognosis for, cancer causatively associated with derangements of chromosome 9p21. Underlying the invention is the discovery that such derangements have their genesis in deletions occurring centromeric to STS 3.21, most often including breakpoints in exon 8 and/or between exons 4 and 5 of the gene which codes for methylthioadenosine phosphorylase. As the cancer and tumor development advance, deletions in 9p21 progress centromerically from the genesis point toward the gene encoding p16. Thus, the method of the invention is performed by determining whether (a) portions of the 9p21 region including and telomeric to STS 3.21 are deleted; and (b) portions of the 9p21 region centromeric to STS 3.21 are deleted; wherein a positive finding in step (a) and a negative finding in step(b) are indicative of a cancer in an early stage of tumor development and a positive finding in step (b) is indicative of a cancer in an advanced stage of tumor development.

27 Claims, 8 Drawing Sheets

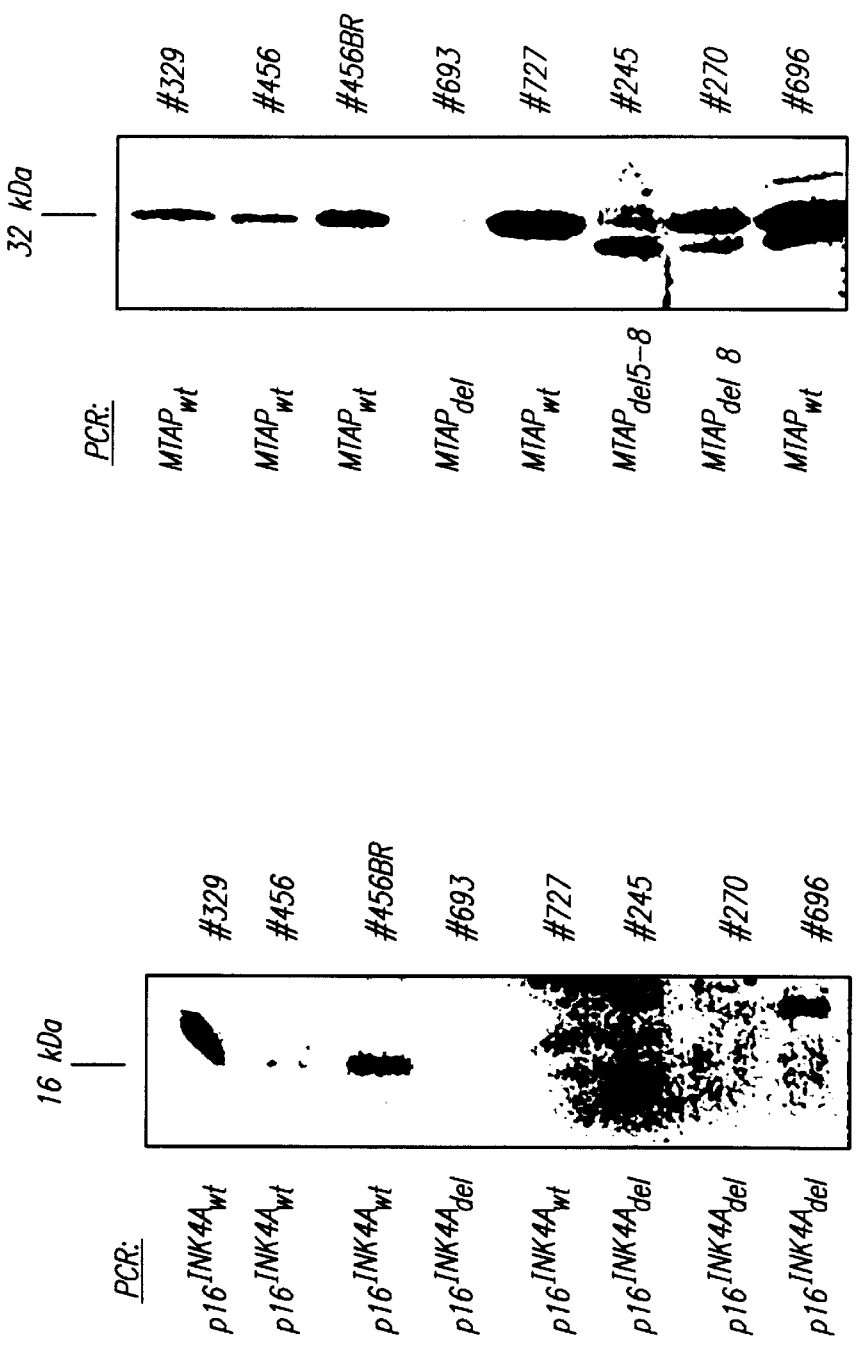

```
   1 CCTGGTCTCG CACTGCTCAC TCCCGCGCAG TGAGGTTGGC AGAGCCACCG
  51 CTCTGTGGCT CGCTTGGTTC CCTTAGTCCC GAGCGCTCGC CCACTGCAGA
 101 TTCCTTTCCC GTGCAGACAT GGCCTCTGGC ACCACCACTA CCGCCGTGAA
 151 GGTGAGATGA GCCCTCCCAG CCGCAGCGGT TCGCCTGCCG GATGCCTTCN
 201 NNNNNNNNNN NNNNNNNNNN NNNNNNNNNN NNNNNNNNNN NNNNNNNNNN
 251 CCTTCAAATG TTTGTTGATT TTTATGGAAG GCTTTGAAAT ATTTGTTGAT
 301 TGATGTTCAG TAATTTTCAG ATTTCAAAAA AATAACTAGG GCTTGGCAGG
 351 AATGGAGAAG AGCATATGAA TAAATGAATT TGCTTAGAAT CTTATTTCTA
 401 ATAAAAATTA CCAAATACAA TAATCTTATA TGTCTTTTTC TGCTCTTAGA
 451 TTGGAATAAT TGGTGGAACA GGCCTGGATG ATCCAGAAAT TTTAGAAGGA
 501 AGAACTGAAA AATATGTGGA TACTCCATTT GGCAAGGTTA ATATCCAACT
 551 TGTGGAGACA TGTTTTNNNN NNNNNNNNNN NNNNNNNNNN NNNNNNNNNN
 601 TTCTCTAAGT TGTATCCTCA GACTCTTCAG ATTCCATGAG TCCTGTTGTG
 651 GTTGAACAAT TATAATTTAC ATACCTGTTT TTTAAATCAC TGAGTTAAAT
 701 GTCATTTTTT TCATTGCATG CAGCCATCTG ATGCCTTAAT TTTGGGGAAG
 751 ATAAAAAATG TTGATTGCGT CCTCCTTGCA AGGTATGGTA NNNNNNNNNN
 801 NNNNNNNNNN NNNNNNNNNN NNNNNNNNNN NNNNNNNNNN NNNNNNNNNN
 851 AAGCTTGATA CTCATCACGG GTTAACAATT TCTTCTCTCC TTCCATAGGC
 901 ATGGAAGGCA GCACACCATC ATGCCTTCAA AGGTCAACTA CCAGGCGAAC
 951 ATCTGGGCTT TGAAGGAAGA GGGCTGTACA CATGTCATAG TGACCACAGC
1001 TTGTGGCTCC TTGAGGGAGG AGATTCAGCC CGGCGATATT GTCATTATTG
1051 ATCAGTTCAT TGACAGGTAA GCAGTCATAC AAAATGCTTT AGGCTATTGT
1101 AGCTGGTCAT TTTCAGCTCA AATGGACGAC NNNNNNNNNN NNNNNNNNNN
1151 NNNNNNNNNN NNNNNNNNNN NNNNNNNNNN NNNNNNNNNN NNNNNNNNNN
1201 GAGGTCGACG GTATCGATAA GCTTTGTAAA CAATTGTCTT TAGCTTATCC
1251 AGAGGAATTG AGTCTGGAGT AAAGACCCAA ATATTGACCT AGATAAAGTT
1301 GACTCACCAG CCCTCGGAGG ATGGAAAGAT GGCCTTAAAA TAAAACAAAC
1351 AAAAACCTTT TTTGCTTTAT TTTGTAGGAC CACTATGAGA CCTCAGTCCT
1401 TCTATGATGG AAGTCATTCT TGTGCCAGAG GAGTGTGCCA TATTCCAATG
```

FIG. 7A

```
1451 GCTGAGCCGT TTTGCCCCAA AACGAGAGAG GTGTGTAGTC TTTCTGGAAG
1501 GTGTACCAGA ATAAATCATG TGGGCTTGGG GTGGCATCTG GCATTTGGTT
1551 AATTGGCAGA CGGAGTGGCC CCATACCCTC ACTCAAGTTT GCTTTGTATT
1601 ATGCAAGTTT ATGGAGAGTT ATTTCCTGTT GCTAATAATT TNNNNNNNNN
1651 NNNNNNNNNN NNNNNNNNNN NNNNNNNNNN NNNNNNNNNN NNNNNNNNNN
1701 AAGTGCAGCC TTAAGTTGTG CATGTGCTAG TATGTTTTGA AGTTTCTGGT
1751 TTTTCTTTTC TAGGTTCTTA TAGAGACTGC TAAGAAGCTA GGACTCCGGT
1801 GCCACTCAAA GGGGACAATG GTCACAATCG AGGGACCTCG TTTTAGCTCC
1851 CGGCAGAAA GCTTCATGTT CCGCACCTGG GGGGCGGATG TTATCAACAT
1901 GACCACAGTT CCAGAGGTGG TTCTTGCTAA GGAGGCTGGA ATTTGTTACG
1951 CAAGTATCGC CATGGGCACA GATTATGACT GCTGGAAGGA GCACGAGGAA
2001 GCAGTAGGTG GAATTCTTTT CTAAGCACAT ATAGCATGGG TTTCTGGGTG
2051 CCAATAGGGT GTCTTAACTG TTTGTTTCTA TTACGTTAGT TTCAGAAAGT
2101 GCCTTTCTAC AAGGTTTTGA AGTTGTTAAT ATTTTCTGTA GTTCCATTGG
2151 AAGGTAAGAA CAAAGATCAA AAGAAAGAAA GAGACACTTT TACCCAAGGA
2201 TCAGTAGTGA AAATAGTACA TTGTAGGCAT GTAGATGTGT TGAGAATCAT
2251 ACTAAGACTT GGGCCTTNNN NNNNNNNNNN NNNNNNNNNN NNNNNNNNNN
2301 NNNNNNNNNN NNNNNNNNNN NNNNNNNNNN NNNNNNNNNN NNNNNNNNNN
2351 GAGCTCCGAA AAATGTTTTA TGACTAGCAG TGGAATTTTA AGTTCTAGTA
2401 ACCTCCAGTG CTATTGTTTC TCTAGGTTTC GGTGGACCGG GTCTTAAAGA
2451 CCCTGAAAGA AAACGCTAAT AAAGCCAAAA GCTTACTGCT CACTACCATA
2501 CCTCAGATAG GGTCCACAGA ATGGTCAGAA ACCCTCCATA ACCTGAAGGT
2551 AAGTGTCAGC CATGGACAAC CAGGCATGTC TGGAGACTCT CTATTGTCTT
2601 CTCCTCTCAC TAGCATCACA CCCGGGGGTC CTCATGTATT TTATGCCAGC
2651 CTANNNNNNN NNNNNNNNNN NNNNNNNNNN NNNNNNNNNN NNNNNNNNNN
2701 CTGTAGAATT TATTTAAAGT GTATGTTTCC TGCGTCCTCA CTTTGATCTA
2751 GAAAATCAAA ATCTGGTTTT TTTTTTAACA AACATCTCAG TAATTACGCC
2801 AACATGTGAA TATCACTGCC TCCTTTCTTC CTTTCAGAAT ATGGCCCAGT
```

*FIG. 7B*

2851 TTTCTGTTTT ATTACCAAGA CATTAAAGTA GCATGGCTGC CCAGGAGAAA
2901 AGAAGACATT CTAATTCCAG TCATTTGGGA ATTCCTGCTT AACTTGAAAA
2951 AAATATGGGA AAGACATGCA GCTTTCATGC CCTTGCCTAT CAAAGAGTAT
3001 GTTGTAAGAA AGACAAGACA TTTGTGTGTA TTAGAGACTC CTGAATGATT
3051 TAGACAACTT CAAAATACAG AAGAAAAGCA AAA

*FIG. 7C*

SEQUENCE LISTING

```
<160> NUMBER OF SEQ ID NOS:  25

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:sense primer

<400> SEQUENCE: 1
agggacctcg ttttatctct tga                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 2
ctagcatttt ctttcggggt ctg                                            23

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:sense primer

<400> SEQUENCE: 3
agttttctgt tttattacca ag                                             22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 4
gtcatttgct tttcttctgt att                                            23

<210> SEQ ID NO 5
<211> LENGTH: 30
<212> TYPE: DNA
<213> ORGANISM: Artificial Sequence
<220> FEATURE:
```

-continued

<223> OTHER INFORMATION: Description of Artificial Sequence:sense primer

<400> SEQUENCE: 5
ggaattctag gctgcggaat gcgcgaggag                                       30

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 6
atcatgacct ggatcgcgcg gcctcccgaa a                                     31

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:sense primer

<400> SEQUENCE: 7
ttcttagaat aatggtat                                                    18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 8
taaggatatt tacatag                                                     17

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:sense primer

<400> SEQUENCE: 9
tcggcggctg cggagagggg gagag                                            25

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 10
tcctccagag tcgcccgcca tcc                                              23

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:sense primer

<400> SEQUENCE: 11

-continued

```
cgattgaaag aaccagagag g                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 12
atggacattt acggtagtgg g                                              21

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:sense primer

<400> SEQUENCE: 13
aaaggagttg gattgtg                                                   17

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 14
ttctcactcc cattttcatc                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:sense primer

<400> SEQUENCE: 15
tgagaactag agcttggaag                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 16
aaccctcctt caaatctgta                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:sense primer

<400> SEQUENCE: 17
aggatgttga agggacattg                                                20

<210> SEQ ID NO 18
```

```
<211> LENGTH: 20
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 18
tgtgttgtgg acctctgtgc                                              20

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:sense primer

<400> SEQUENCE: 19
aagaagatgc ggctgactgt cgagccacat                                   30

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 20
tctcatggtt cacacccatg acgaacatg                                    29

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:sense primer

<400> SEQUENCE: 21
atggcctctg gcaccaccac                                              20

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:anti-sense
      primer

<400> SEQUENCE: 22
ctgtcaatga actgatcaat aatgac                                       26

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence:sense primer

<400> SEQUENCE: 23
gaccactatg agacctcagt ccttctatga tg                                32

<210> SEQ ID NO 24
<211> LENGTH: 32
<212> TYPE: DNA
<213> ORGANISM: Artificial Sequence
<220> FEATURE:
```

<223> OTHER INFORMATION: Description of Artificial Sequence:anti-sense
      primer

<400> SEQUENCE: 24
ttaatgtctt ggtaataaaa cagaaaactg gg                                    32

<210> SEQ ID NO 25
<211> LENGTH: 3083
<212> TYPE: DNA
<213> ORGANISM: Homo sapiens
<220> FEATURE:
<223> OTHER INFORMATION: genomic sequence for methylthioadenosine
      phosphorylase (MTAP) gene
<221> NAME/KEY: modified_base
<222> LOCATION: (1)..(3083)
<223> OTHER INFORMATION: n = unknown
<221> NAME/KEY: exon
<222> LOCATION: (119)..(151)
<223> OTHER INFORMATION: exon 1
<221> NAME/KEY: exon
<222> LOCATION: (450)..(536)
<223> OTHER INFORMATION: exon 2
<221> NAME/KEY: exon
<222> LOCATION: (724)..(782)
<223> OTHER INFORMATION: exon 3
<221> NAME/KEY: exon
<222> LOCATION: (899)..(1066)
<223> OTHER INFORMATION: exon 4
<221> NAME/KEY: exon
<222> LOCATION: (1378)..(1480)
<223> OTHER INFORMATION: exon 5
<221> NAME/KEY: exon
<222> LOCATION: (1764)..(1953)
<223> OTHER INFORMATION: exon 6
<221> NAME/KEY: exon
<222> LOCATION: (2426)..(2548)
<223> OTHER INFORMATION: exon 7
<221> NAME/KEY: exon
<222> LOCATION: (2838)..(2876)
<223> OTHER INFORMATION: exon 8

<400> SEQUENCE: 25
cctggtctcg cactgctcac tcccgcgcag tgaggttggc acagccaccg ctctgtggct        60
cgcttggttc cctttagtccc gagcgctcgc ccactgcaga ttcctttccc gtgcagacat     120
ggcctctggc accaccacta ccgccgtgaa ggtgagatga gccctcccag ccgcagcggt      180
tcgcctgccg gatgccttcn nnnnnnnnn nnnnnnnnnn nnnnnnnnnn nnnnnnnnnn       240
nnnnnnnnnn ccttcaaatg tttgttgatt tttatggaag gctttgaaat atttgttgat     300
tgatgttcag taattttcag atttcaaaaa ataactagg gcttggcagg aatggagaag      360
agcatatgaa taaatgaatt tgcttagaat cttatttcta ataaaaatta ccaaatacaa     420
taatcttata tgtctttttc tgctcttaga ttggaataat tggtggaaca ggcctggatg    480
atccagaaat tttagaagga agaactgaaa aatatgtgga tactccatt ggcaaggtta    540 atatccaact tgtggagaca tgttttnnnn nnnnnnnnnn nnnnnnnnnn nnnnnnnnnn    600
ttctctaagt tgtatcctca gactcttcag attccatgag tcctgttgtg gttgaacaat     660
tataatttac atacctgttt tttaaatcac tgagttaaat gtcattttt tcattgcatg      720 cagccatctg atgccttaat tttggggaag ataaaaatg ttgattgcgt cctccttgca     780
aggtatggta nnnnnnnnnn nnnnnnnnnn nnnnnnnnnn nnnnnnnnnn nnnnnnnnnn    840
nnnnnnnnna aagcttgata ctcatcacgg gttaacaatt tcttctctcc ttccataggc    900
atggaaggca gcacaccatc atgccttcaa aggtcaacta ccaggcgaac atctgggctt    960
tgaaggaaga gggctgtaca catgtcatag tgaccacagc ttgtggctcc ttgagggagg   1020

-continued

```
agattcagcc cggcgatatt gtcattattg atcagttcat tgacaggtaa gcagtcatac    1080
aaaatgcttt aggctattgt agctggtcat tttcagctca aatggacgac nnnnnnnnnn    1140
nnnnnnnnnn nnnnnnnnnn nnnnnnnnnn nnnnnnnnnn nnnnnnnnnn nnnnnnnnnn    1200
gaggtcgacg gtatcgataa gctttgtaaa caattgtctt tagcttatcc agaggaattg    1260
agtctggagt aaagacccaa atattgacct agataaagtt gactcaccag ccctcggagg    1320
atggaaagat ggccttaaaa taaaacaaac aaaaaccttt tttgctttat tttgtaggac    1380
cactatgaga cctcagtcct tctatgatgg aagtcattct tgtgccagag gagtgtgcca    1440
tattccaatg gctgagccgt tttgccccaa aacgagagag gtgtgtagtc tttctggaag    1500
gtgtaccaga ataaatcatg tgggcttggg gtggcatctg gcatttggtt aattggcaga    1560
cggagtggcc ccatacccctc actcaagttt gctttgtatt atgcaagttt atggagagtt    1620
atttcctgtt gctaataatt tnnnnnnnnn nnnnnnnnnn nnnnnnnnnn nnnnnnnnnn    1680
nnnnnnnnnn nnnnnnnnnn aagtgcagcc ttaagttgtg catgtgctag tatgttttga    1740
agtttctggt ttttcttttc taggttctta tagagactgc taagaagcta ggactccggt    1800
gccactcaaa ggggacaatg gtcacaatcg agggacctcg ttttagctcc cgggcagaaa    1860
gcttcatgtt ccgcacctgg ggggcggatg ttatcaacat gaccacagtt ccagaggtgg    1920
ttcttgctaa ggaggctgga atttgttacg caagtatcgc catgggcaca gattatgact    1980
gctggaagga gcacgaggaa gcagtaggtg gaattctttt ctaagcacat atagcatggg    2040
tttctgggtg ccaatagggt gtcttaactg tttgtttcta ttacgttagt ttcagaaagt    2100
gcctttctac aaggtttga agttgttaat attttctgta gttccattgg aaggtaagaa    2160
caaagatcaa aagaaagaaa gagacacttt tacccaagga tcagtagtga aaatagtaca    2220
ttgtaggcat gtagatgtgt tgagaatcat actaagactt gggccttnnn nnnnnnnnn    2280 nnnnnnnnnn nnnnnnnnnn nnnnnnnnnn nnnnnnnnnn nnnnnnnnnn nnnnnnnnnn    2340
nnnnnnnnnn gagctccgaa aaatgtttta tgactagcag tggaattta agttctagta    2400 acctccagtg ctattgtttc tctaggtttc ggtggaccgg gtcttaaaga ccctgaaaga    2460
aaacgctaat aaagccaaaa gcttactgct cactaccata cctcagatag ggtccacaga    2520
atggtcagaa accctccata acctgaaggt aagtgtcagc catggacaac caggcatgtc    2580
tggagactct ctattgtctt ctcctctcac tagcatcaca cccgggggtc ctcatgtatt    2640
ttatgccagc ctannnnnnn nnnnnnnnnn nnnnnnnnnn nnnnnnnnnn nnnnnnnnnn    2700
ctgtagaatt tatttaaagt gtatgtttcc tgcgtcctca ctttgatcta gaaaatcaaa    2760
atctggtttt tttttttaaca aacatctcag taattacgcc aacatgtgaa tatcactgcc    2820
tcctttcttc ctttcagaat atggcccagt tttctgtttt attaccaaga cattaaagta    2880
gcatggctgc ccaggagaaa agaagacatt ctaattccag tcatttggga attcctgctt    2940
aacttgaaaa aaatatggga aagacatgca gctttcatgc ccttgcctat caaagagtat    3000
gttgtaagaa agacaagaca tttgtgtgta ttagagactc ctgaatgatt tagacaactt    3060
caaaatacag aagaaaagca aaa                                            3083
```

METHOD FOR EARLY DIAGNOSIS OF, AND DETERMINATION OF PROGNOSIS IN, CANCER

STATEMENT REGARDING RELATED APPLICATIONS

This application is a utility conversion of U.S. Provisional Patent Application Ser. No. 60/090,411, filed on Jun. 23, 1998, the priority of which is claimed.

STATEMENT REGARDING GOVERNMENT SUPPORT

The work underlying this invention was supported by a grant from the National Institutes of Health, Grant Numbers 5 UO1 CA64976 and 5 R21 CA68260. The Government may have certain rights in the invention.

BACKGROUND OF THE INVENTION

1. Field of the Invention

The invention relates to methods for early diagnosis and staging of cancer which is causatively related to derangements of chromosomal 9p21 in mammals.

2. History of the Related Art

The chromosomal region 9p21 harbors five different genes within about 120 kb: the tumor suppressor genes p15IINK4B (CDKN4B, hereafter "p15") with its alternative spliced form p10, p16INK4A (CDKN2A, a key regulator of the G1-phase of the cell cycle and growth control, hereafter "p 16") and p19ARF (which acts via a p53 dependent pathway to block cell cycle progression), as well as the gene for the metabolic enzyme methylthioadenosine phosphorylase (MTAP).

Homozygous deletion is the most important mechanism of inactivation of all three genes. While somatic and germline mutations have been described for p16, they seem to be very rare in the other two genes. A third mechanism of inactivation is hypermethylation of CpG-islands in the promoter region of both p15 and p16, which results in silencing of transcription. No relationship between hypermethylation and tumor grade has been observed.

Studies of tumor cell lines and gross primary tumors reveal that homozygous deletions of p16 are found in 10–60% of brain tumors, depending on the tumor stage and histology. Homozygous deletions of p16 are also present in melanomas, lung cancers, malignant mesotheliomas, bladder cancers, pancreatic carcinomas, ovarian carcinomas, head and neck cancers, chondrosarcomas, esophageal squamous cell carcinomas, T-cell acute lymphoblastic leukemias, and other primary lymphoid malignancies.

Loss of heterozygosity (LOH) as well as hemi- and homozygous deletions of the 9p21 region encompassing the p16INKA4 gene and MTAP genes have been described in a variety of human tumors, primarily based on analysis of tumor cell lines, including acute lymphoblastic leukemia (ALL), melanoma, ovarian cancer, glioma, head and neck cancer, bladder cancer, chondrosarcoma, small cell and non-small cell lung cancer (NSCLC). In general, it has been widely concluded that the portion of 9p21 where the p16 INK4A gene resides is the point at which derangements in the region of 9p21 between that and the MTAP gene begin, indicating that p16 would be a marker for cancer at early and more advanced stages of tumor development.

SUMMARY OF THE INVENTION

The invention provides a method for differentiating among stages of tumor development which is causatively related to derangements of chromosomal region 9p21 in mammals. More particularly, the invention provides a framework for both early diagnosis of such cancers and prognosis based on the stage of tumor development. In the paradigm provided by the invention, derangements of 9p21 in many cancers begin at the MTAP gene locus at the onset of tumor development and progress centromerically toward the p16 gene locus as tumor development advances, as represented in the pictorial below:

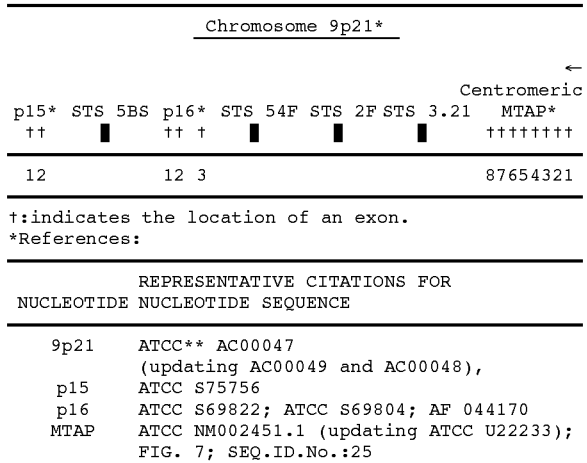

†:indicates the location of an exon.
*References:

| NUCLEOTIDE | REPRESENTATIVE CITATIONS FOR NUCLEOTIDE SEQUENCE |
|---|---|
| 9p21 | ATCC** AC00047 (updating AC00049 and AC00048), |
| p15 | ATCC S75756 |
| p16 | ATCC S69822; ATCC S69804; AF 044170 |
| MTAP | ATCC NM002451.1 (updating ATCC U22233); FIG. 7; SEQ.ID.No.:25 |

**ATCC = American Type Culture Collection

According to the method of the invention, a model pattern of deletion of portions of chromosome 9p21 ("staging reference"; see, e.g., FIG. 1) is used as a reference for comparison to 9p21 in samples of cells which are suspected of, or confirmed as, being cancerous. The sample cells are analyzed for the presence of deletions and breakpoints in 9p21. The deletion pattern identified in the sample cells is compared against the staging reference, in which the presence or absence of certain deletions and breakpoints in 9p21 are correlated to the stage of development of cancer in the sample cell population.

The data upon which the staging reference is based are derived from analysis of 9p21 in histological grade, paraffin-embedded samples of human tumors at various stages of tumor development identified according to conventional staging techniques. Unlike the tumor cell lines used in previous analyses of 9p21 derangements, the unique tissue samples utilized as the basis for development of the staging reference include very early stage tumors as well as advanced stage tumors.

Surprisingly, analysis of the tissue samples revealed that, in contrast to widely held perception, the p16INK4a (p16) gene is not the starting point for the 9p21 derangements observed in cancer cell lines and advanced primary tumors. Rather, the derangement starting point in many tumor cells lies just centromeric to exon 8 of the MTAP gene (telomeric to sequence tagged site [STS] 3.21), while in others the first breakpoint is within the MTAP gene, between exons 4 and 5. As tumor development progresses, deletions within 9p21 advance centromerically toward inclusion of all or part of the p16 coding sequence, and may also advance telomerically toward of all or part of the MTAP coding sequence. An additional fragile site lying between p16 and p15INK4b (p15) can lead to deletion of a portion of 9p21 in more advanced tumor cells. Thus, p16 deletion alone is not a reliable marker for either early diagnosis or prognostic staging of cancer, both of which can be accomplished by use of the staging reference of the invention.

The invention also provides methods and reagents for use in early diagnosis of cancer through hybridization to early deletion points in 9p21.

BRIEF DESCRIPTION OF THE DRAWINGS

FIG. 5(a) is a blot radiograph depicting p16 expression in xenograft brain tumors while FIG. 5(b) is a blot radiograph depicting MTAP expression in xenograft brain tumors.

FIG. 7 is a genomic nucleotide sequence for the MTAP gene; with the exons highlighted by underlining.

DETAILED DESCRIPTION OF THE INVENTION

Figure 1:
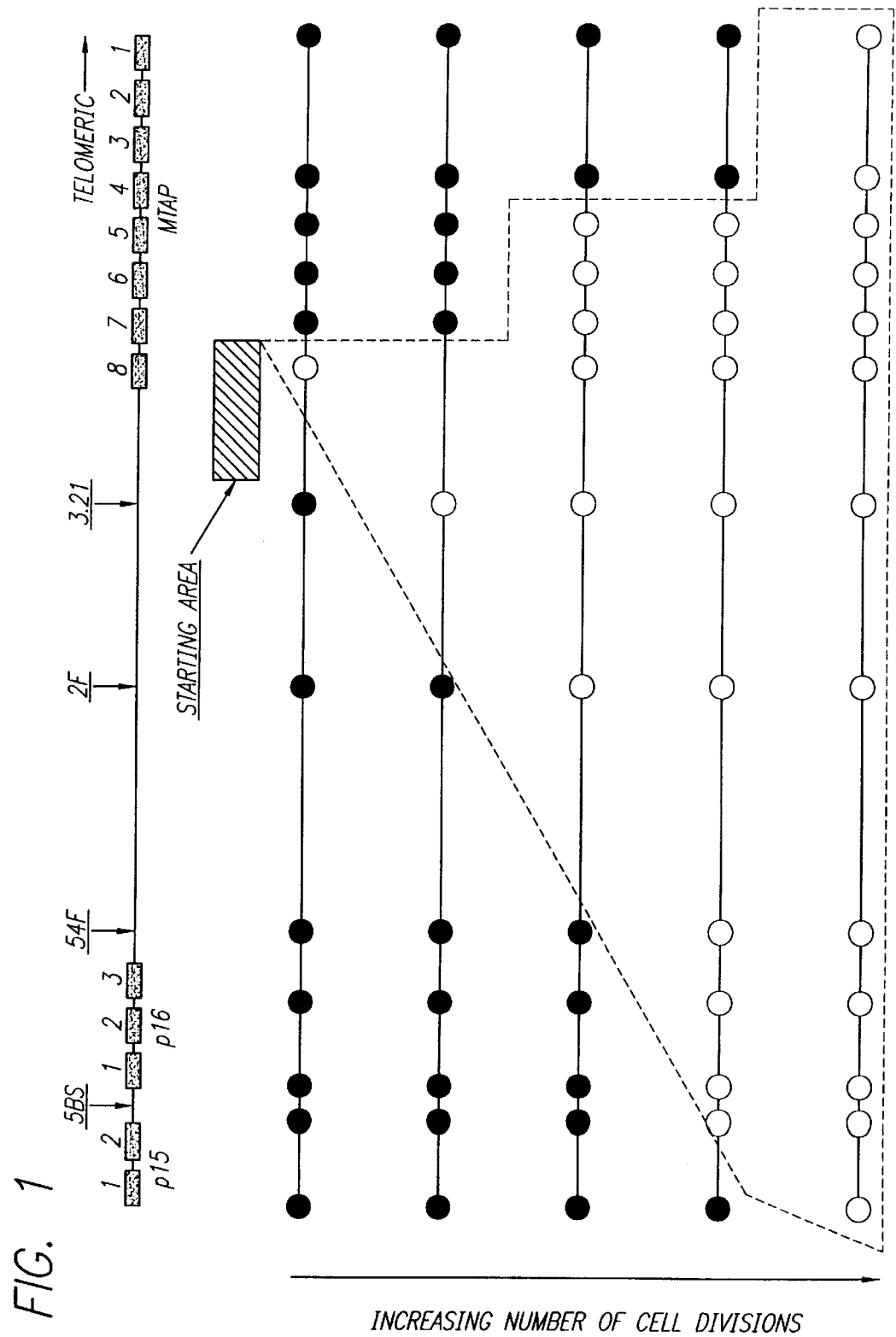
FIG. 1 is a graphical representation of the staging reference of the invention, wherein the dotted line indicates the progression of derangements in 9p21, solid circles (•) indicate the absence of a deletion (normal gene structure) and open circles (○) indicate the occurrence of a deletion. The figure uses the breakpoint in MTAP gene exon 8 as the start point for 9p21 derangement and therefore represents (determined as described in the Detailed Description) a common paradigm in early cancer development.

The invention provides a method for diagnosis of, and determining a prognosis for, cancer causatively associated with derangements of chromosome 9p21. Underlying the invention is the discovery that such derangements have their genesis in deletions occurring centromeric to STS 3.21, most often including breakpoints in exon 8 and/or between exons 4 and 5 of the gene which codes for methylthioadenosine phosphorylase;(MTAP).

As the cancer and, tumor development advance, deletions in 9p21 progress centromerically from the genesis point toward the gene encoding p16. Thus, the method of the invention is performed by determining whether (a) portions of the 9p21 region including and telomeric to STS 3.21 are deleted; and (b) portions of the 9p21 region centromeric to STS 3.21 are deleted; wherein a positive finding in step (a) and a negative finding in step (b) are indicative of a cancer in an early stage of tumor development and a positive finding in step (b) is indicative of a cancer in an advanced stage of tumor-development.

In this respect,-the phrase "an early stage of tumor development" refers to tumors of histologic grade III or lower, with the majority falling within histologic grades I and II. Furthermore,the phrase "an advanced stage of tumor development" refers to tumors of histologic grade III or higher., with the majority falling within histologic grade IV. In the invention, histologic grade III is considered as a portal grade, a finding for which is indicative of progressive tumor development from an early to an advanced stage. Histologic evaluation of a tumor may be utilized to determine the exact grade into which a particular tumor whose stage is identified according to the method of the invention falls.

The data described herein are derived from investigation into the scope of 9p21 deletions in 95 brain tumors of different stages (of both astrocytic and oligodendroglial origin), as well as in non-small cell lung cancer (NSCLC). These types of cancer are representative of those associated with derangements in 9p21.

Of the brain tumors, only eleven glioblastomas had p16 deletions without MTAP deletions. Unexpectedly, eight out of 95 tumors (8%) showed homozygous MTAP deletions without p16 deletions and these comprised 23% of the histologic grade I–III specimens. In fourteen cases, including 12 glioblastomas, both p16 and MTAP were deleted. No grade I–III tumor had an isolated p16 deletion, establishing that the p16 gene is not the genesis of 9p21 derangements in these cancers.

Of the NSCLC samples (including 25 adenocarcinomas (50%), 21 squamous cell carcinomas (42%) and 4 large cell carcinomas (8%)), homozygous deletions of MTAP exon 8 could be detected in 19 of 50 NSCLC samples (38%). Adenocarcinoma (11 of 25, 44%) showed a higher deletion frequency than squamous cell carcinoma (6 of 21, 29%). In contrast, homozygous p16 deletions were detected in only 9 of 50 (18%) samples using specific primers for p16 exon 1. No difference between the histological subtypes and p16 deletion frequency was observed. Interestingly; among the 10 samples with MTAP deletions but intact p16 exon 1 (evaluated with primers specific for p16 exon 3, the exon nearest to MTAP exon 8; see Table 1 below), none of the samples had a deletion of the p16 exon 3 coding region.

To localize the deletion breakpoints which lead to the inactivation of the genes, the region between p15 and MTAP was mapped using specific primers for recently defined sequence tagged sites (STS) as well as for the different exons of the genes. In summary, common breakpoints within the MTAP gene occurred between exons 4 and 5 and between exons 7 and 8. Similar breakpoints were observed in brain tumor xenografts (5 childhood and 11 adult brain tumors) propagated in nude mice, although deletions of p16 and MTAP in childhood tumors were rare in comparison to the occurrence of p15 deletions.

Western blot analysis showed that the MTAP protein was present in all tested tumors that contained the MTAP gene, whereas two tumors with an intact p16 gene lacked detectable p16 protein. Xenografts with breakpoints between MTAP exons 7/8 and exons 4/5 produced immunoreactive MTAP proteins of about 32 kDa and 28 kDa, respectively, and MTAP mRNA. These results demonstrate that homozygous MTAP without p16 deletions are common in low-grade gliomas.

The staging reference model (FIG. 1) for cancer progression from a deletion at the breakpoint at MTAP gene exon 8 represents a common paradigm for early cancer development in gliomas and other cancers associated with 9p21 chromosomal derangements. Among adult tumors, deletions at breakpoints in MTAP exon 8 and/or between MTAP exons 4 and 5, without involvement of 9p21 centromeric to MTAP exon 8, exclusively occur in low-grade tumors (e.g., stage III and below in gliomas). Detection of this phenotype in a tumor therefore evidences early cancer development and, presumably, greater susceptibility to treatment. In contrast, derangements of 9p21 involving deletions of the MTAP gene and regions centromeric thereto, including the p16 gene, evidence advanced tumor development (mirroring the condition present in tumor cell lines). In contrast, MTAP/p16 combination deletions are relatively rare and are preceded by the more predominant deletion of p15.

An important result of the deletion analysis in brain tumors was that twenty-three percent of the grade II–III gliomas were MTAP negative and p16 positive, compared to only 2% of the grade IV tumors (p=0.0005 by chi square analysis). The single glioblastoma with an isolated MTAP deletion had a p16 gene dosage level closest to the negative cutoff point, among all the tumors analyzed. Moreover, there was a positive correlation between the size of the deletions and the grade of the tumor, with large deletions involving p16 predominantly confined to glioblastomas.

Twenty-three out of the 25 p16 deletions were in grade IV tumors. This is in accordance with previous findings. Despite differences in the exact percentages of p16 deletions detected in different studies, it seems clear that homozygous deletion of this cdk-inhibitor is a feature of high-grade gliomas. In addition, p16 is more often deleted in astrocytic than in non-astrocytic tumors.

Although the invention is not limited by any theory concerning the genetic causes for the findings described herein, the staging reference (exemplified in FIG. 1) could explain the evolution of glioblastomas in the adult. According to this scheme, an initial, small deletion occurs close to MTAP exon 8, and inactivates a functional motif, such as a new gene, another INK4 exon, or a promoter/enhancer site for p16 or p19ARF. This deletion may cause genetic instability in the 9p21 region, leading to the loss of additional chromosomal material during further cell doublings. The new breakpoints would tend to occur at fragile sites, which explains the presence of distinct breakpoints, e.g., between MTAP exons 4 and 5, and between p15 and p16.

Figure 3:
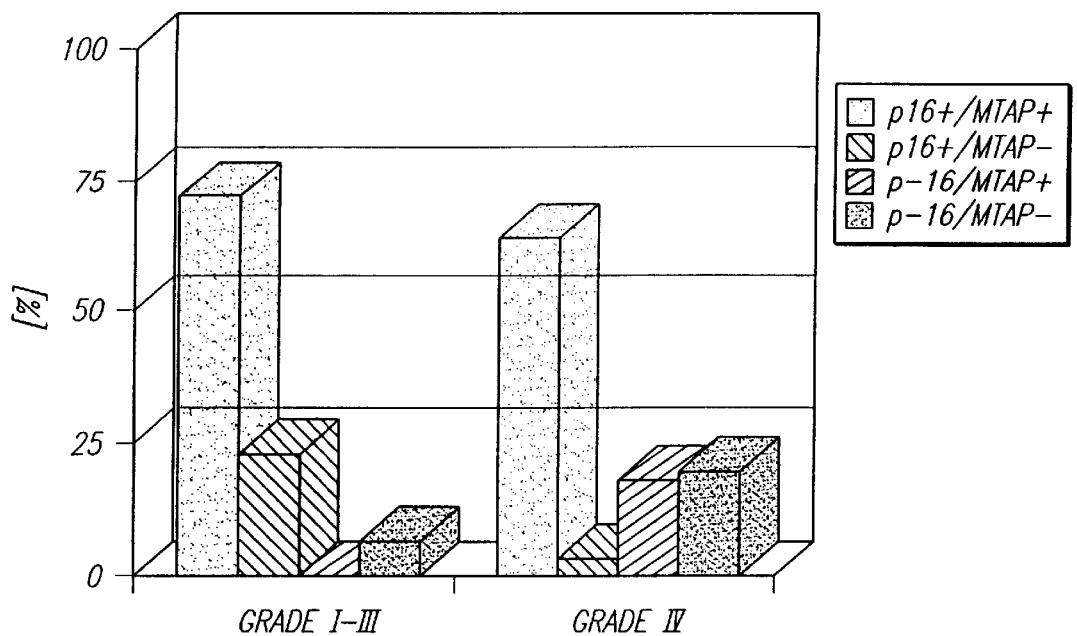
FIG. 3 is a chart which relates the occurrence of a homozygous deletion occurring in the MTAP gene with or without involvement of the p16 coding sequence, as well as normal 9p21 spanning the sites of these genes, with the stage of cancer in tested tumor samples obtained as described in the Detailed Description. In the figure legend, (+) refers to the absence of a deletion in the indicated region of 9p21 (normal gene structure) and (−) refers to the occurrence of a deletion in the region. Cancer grade is indicated along the bottom axis of the figure.
Figure 6:
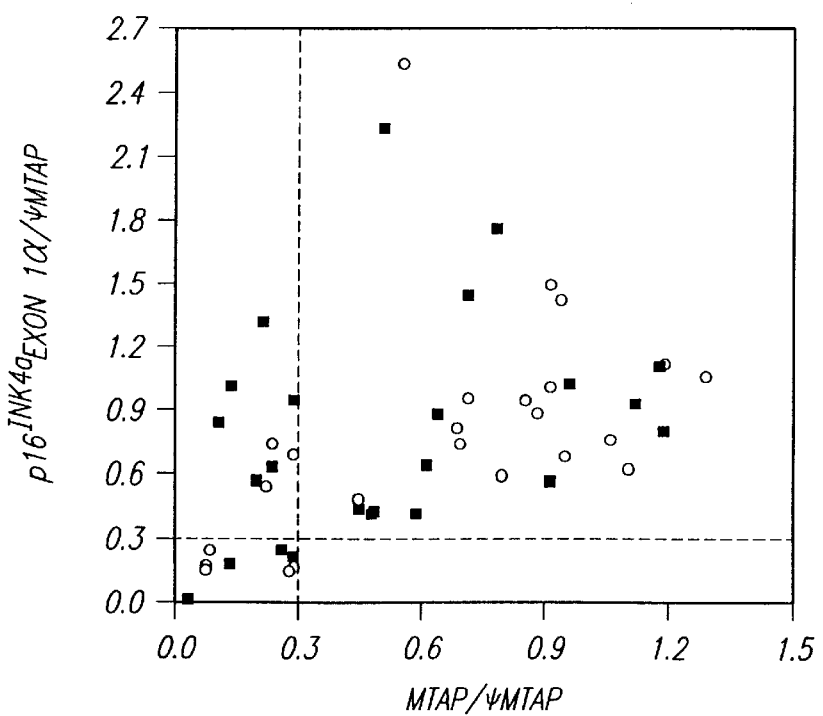
FIG. 6 is a graph correlating MTAP/control gene (MTAPψ) and p16/control gene dosage rations in adenosarcomas (■) and in squamous and large cell carcinomas (○).

With respect to childhood cancers, the expression of p16 increases as fibroblasts approach senescence. On the other hand, neither p16 nor p19ARF is highly expressed in embryonic tissues, whereas p15 (as well as the INK4 genes p18INK4c and p19INK4d) expression has been detected in fetal tissues of mouse and man. The p16 gene locus was intact in 4 out of 5 of childhood glioma xenografts studied, whereas the p15 locus was deleted in all but one of the tumors (FIG. 3). These preliminary results are consistent with the concept that p15, rather than p16, plays a role in early organogenesis of the brain and that p15 inactivation is a frequent step in the development of childhood gliomas.

These data were developed as described further below. The staging model set forth in FIG. 1 provides a common paradigm for the brain tumors studies and relates 9p21 derangements and their progression from exon 8 of the MTAP gene to clinical grades of tumors. Detection of derangements in 9p21 matched to the staging reference reveal both the probable presence of a tumor (even, significantly, at a stage of development not detectable on gross examination) and its probable grade of advancement. Those of ordinary skill in the art will be familiar with the clinical significance from a prognostic viewpoint of determining the grade of particular cancers, as set forth in, for example, Ginsberg, *Oncology*, 12(1 Suppl. 2):51–54 (1998) [NSCLC]; Ross, *Curr. Opin. Oncology*, 10:153–161 (1998) [melanoma]; Kreth, et al., *Cancer*, 79:370–379 (1997) 79:370–379 [gliomas]; and, Shaw, et al., *J. Neurooncol.*, 3 1:273–278 (1997) [gliomas].

Further, with knowledge provided by the invention of the most common genesis points for 9p21 derangements (exon 7 of the MTAP gene [FIG. 7; SEQ. ID. No.: 25]; the junction of exons 4 and 5 of the MTAP gene [id.], as well as a point between STS 3.21 and MTAP exon 8 FIG. 8; SEQ. ID. No. 25, early detection and correlation to grade of advancement of cancers other than those specifically studied herein can be performed by those of ordinary skill in the art, especially through utilization of the techniques described herein for obtaining histological-grade specimens of tumors at early stages of development and application of the highly sensitive PCR-ELISA technique for analysis of such specimens which is described herein.

Examples illustrating practice of the invention and providing data in proof of the principles underlying the invention are provided below. Neither these examples nor the disclosure above should be regarded as limiting the scope of the invention, which is defined by the claims appended hereto.

In the Examples, standard abbreviations (e.g., "ml" for milliliters; "n" for sample size and the like) are used unless otherwise noted.

EXAMPLE I

Method for Obtaining Histological-grade Specimens of Tumors at Early Stages of Development Tumor Samples. Ninety-five malignant brain tumors excised from human patients and provided to the glioma marker network were obtained from the Mayo clinic, Rochester, Minn. (n=19), the Johns -Hopkins University, Baltimore, Ma. (n=51), and the University of California at San Diego (n=25). Tumors were either frozen at −70° C. directly after excision without further fixation (n=7 1), or were fixed in 10% neutral buffered formalin for 24–48 hours, then were immediately embedded in histologic grade paraffin according to standard procedures (n=24). Paraffin blocks were stored at room temperature until assayed. Representative slides were available from all paraffin-embedded tissue blocks and were examined microscopically to determine the tumor-rich parts of each specimen.

In addition, 16 xenograft tumors (established at Duke University) were investigated. The xenografts were derived from both childhood (n=5) and adult (n=11) primary malignant gliomas, and were propagated in nude mice to a diameter of approximately 2 cm. Excised tumors were stored at −70° C. until analyzed.

NSCLC tumors were obtained from 50 randomly selected male human patients having a median age of 65 years. The tumors were paraffin-embedded as described above.

DNA Extraction. DNA from unfixed samples as well as from xenograft tumors was extracted using a Qiagen Tissue Kit (Qiagen, Chatsworth, Calif.) according to the manufacturer's protocol. Between 25–75 mg of tissue were used in each extraction procedure. DNA was measured using a GeneQuant spectrophotometer (Pharmacia, Freiburg, Germany). DNA samples were stored at a concentration of 10 ng/µl at −20° C. until used for PCR.

DNA from fixed tissues was extracted either from the paraffin-block or from 5 µm sections as follows: The top 100 µm of each paraffin block was shaved and discarded to avoid potential sample contamination with extraneous DNA adhering to the block surface during storage. Microscopically identifiable regions of tumor were scratched off the block to a depth of about 5–10 µm with a sterile scalpel blade or needle and placed in a sterile microcentrifuge tube. Alternatively, tumor-rich regions were scratched off the slide after identification in the representative H&E stained slide. Specimens were deparaffinized by incubation twice for 10 minutes in octane. To remove any remaining octane, the tissue pellets were washed twice with 100% ethanol and dried. Further DNA isolation was performed using a Qiagen Tissue Kit with the following modifications: the dried tissue pellet was resuspended in 320 µl ATL lysis buffer and 40 µl proteinase K (Sigma) stock solution (20 mg/ml) was added. Samples were then incubated at 37° C. for 96 h with further addition of 40 µl proteinase K at 48 h. After digesting contaminating RNA with 2 mg/ml RNase A (Sigma, St. Louis, Mo.), DNA was then isolated by elution with 200µ 110 mM Tris-HCL, pH 9.0.

EXAMPLE II

PCR-ELISA Analysis of Tumor Samples

Polymerase Chain Reaction (PCR). PCR-ELISAs were performed generally as described in Barker, et al., *J. Neuro-Oncol.*, 31:17–23 (1997) and in Perry, et al., *J. Neuropath. Exp. Neurol.*, 56: 999–1008 (1997), the disclosures of which are incorporated herein by reference. A total of 50 ng of DNA isolated from each sample was used for amplification.

The recently cloned pseudogene of MTAP (ΨMTAP) localized to chromosome 3q28, served as a control gene. Primers for p16INK4B exon 1, p16 exon 1α and exon 3, MTAP exon 8, and ΨMTAP, and for the sequence tagged sites 5B5 54F, 2F, 3.21, are listed in Table 1. Primers were selected to amplify exon 1 of p16 and exon 8 of MTAP. Primer sequences used to amplify MTAP exons 1–7 have been previously published. All primer pairs were designed to amplify PCR products of similar length between 197–250 bp, and all sense primers were biotinylated at the 5' end (Integrated DNA Technology, Coralville, Iowa).

TABLE 1

Primer Sequences Used for PCR and RT-PCR

| Marker | Sense Primer | Anti-sense Primer | Product Length |
|---|---|---|---|
| ΨMTAP | 5'-AGGGACCTC GTTTTATCTC TTGA 3' (SEQ ID NO.:1) | 5'-CTAGCATT TTCTTTCGGGGTCTG-3' (SEQ ID NO.:2) | 216 bp |
| MTAP exon 8 | 5'-AGTTTTC TGTTTTATTACCAA G-3' (SEQ ID NO.:3) | 5'-GTCATTTGCTTTTCTTCTGTAT T-3' (SEQ ID NO.:4) | 240 bp |
| P15 exon 1 | 5'-GGAATTCTAGGCTG CGGAATGCGCGAG GAG-3' (SEQ ID NO.:5) | 5'-ATCATGACCTGGATCGCGCG GCCTCCCGAAA-3' (SEQ ID NO.:6) | 179 bp |
| STS 5BS* | 5'-TTCTTAGAATAATG GTAT-3' (SEQ ID NO.:7) | 5'-TAAGGATATTTACATAG-3' (SEQ ID NO.:8) | 181 bp |
| P16 exon 1α** | 5'-TCGGCGGCTGCGG AGAGGGGGAGAG-3' (SEQ ID NO.:9) | 5'-TCCTCCAGAGTCGCCCGCCAT CC-3' (SEQ ID NO.:10) | 250 bp |
| P16 exon 3 | 5'-CGATTGAAAGAAC CAGAGAGG-3' (SEQ ID NO.:11) | 5'-ATGGACATTTACGGTAGTGG G-3' (SEQ ID NO.:12) | 196 bp |
| STS 54F | 5'-AAAGGAGTTGG ATTGTG-3' (SEQ ID NO.:13) | 5'-TTCTCACTCCCATTTTCATC-3' (SEQ ID NO.:14) | 184 bp |
| STS 2F | 5'-TGAGAACTAGAGCT TGGAAG-3' (SEQ ID NO.:16) | 5'-AACCCTCCTTCAAATCTGTA-3' (SEQ ID NO.:16) | 248 bp |
| STS 3.21 | 5'-AGGATGTTGAAGG GACATTG-3' (SEQ ID NO.:17) | 5'TGTGTTGTGGACCTCTGTG C-3' (SEQ ID NO.:18) | 200 bp |
| GAPDH | 5'-AAGAAGATGCGGC | 5'-TCTCATGGTTCACACCCATGA | 510 bp |

TABLE 1-continued

Primer Sequences Used for PCR and RT-PCR

| Marker | Sense Primer | Anti-sense Primer | Product Length |
|---|---|---|---|
| | TGACTGTCGAGCCA CAT-3' (SEQ ID NO.:19) | CGAACATG-3' (SEQ ID NO.:20) | |
| MTAP exons 1–4 | 5'-ATGGCCTCTGGCAC CACCAC-3' (SEQ ID NO,:21) | 5'-CTGTCAATGAACTGATCAATA ATGAC-3' (SEQ ID NO.:22) | 347 bp |
| MTAP exons 5–8 | 5'-GACCACTATGAGA CCTCAGTCCTTCTA TGATG-3' (SEQ ID NO.:23) | 5'-TTAATGTCTTGGTAATAAAAC AGAAAACTGGG-3' (SEQ ID NO.:24) | 505 bp |

*Annealing temperature 45° C.
**Annealing temperature: 64° C.

A standard curve was established for each amplified sequence using DNA isolated from the normal lung fibroblast cell line WI-38 (for unfixed samples), or from formalin-fixed, paraffin-embedded normal placenta (for formalin-fixed, paraffin-embedded tumor samples). Zero to 100 ng of control DNA were amplified in each experiment to show the linearity of the PCR reaction and to provide a standard for comparison of amplified tumor sample DNA to normal DNA products. PCR was performed in a total of 50 $\mu$l containing normal or sample DNA, 2.0 mM MgCl2, 2.0 $\mu$l digoxigenin PCR Mix (200 $\mu$M each of dATP, dCTP, and dGTP, 190 $\mu$M dTTP and 10 $\mu$M digoxigenin-dUTP) (Boehringer Mannheim, Indianapolis, Ind.), 7.5–15 pmol of each primer, and SU AmpliTaq Gold™ DNA Polymerase (Perkin Elmer, Branchburg, N.J.) in the reaction buffer provided by the supplier.

Due to a very high GC content of p16 exon 1α, amplification was performed in a reaction mixture containing 5% dimethylsulfoxide (DMSO). Samples were amplified through 27 cycles (fresh tissue) or 29–33 cycles (paraffin-embedded tissues) in a Perkin Elmer thermal cycler using the following parameters: initial denaturation at 94° C. for 5 min, then 27 (29–33, respectively) cycles of 94° C. denaturation for 1 min, annealing at 59° C. for 1 min (64° in case of p16 exon 1α), polymerization at 72° C. for 1 min and a final extension step at 72° C. for 7 min.

Ten $\mu$l of the PCR reactions were analyzed by electrophoresis at 100 V for 45 min in a 2% agarose gel in Tris-borate buffer containing 2 mM EDTA and 0.4 $\mu$g/ml ethidium bromide. Gels were photographed and in some experiments scanned. The intensities of the bands were analyzed using standard software.

Enzyme-Linked Immunosorbent Assay (ELISA). All samples were analyzed for p16 and MTAP deletions in a subsequent ELISA using primers for p16 exon 1 and exon 3, and MTAP exon 8. Polyvinyl microwell plates (Becton-Dickinson, Oxnard, Calif.) were pretreated with glutaraldehyde 0.1% at room temperature for 20 min, washed with PBS, and then coated with streptavidin 0.1 mg/ml (Sigma, St; Louis, Mo.) for 2 h at 37° C. Wells were washed with PBS, then filled with a 0.2 mg/ml sodium borohydrate solution for 10 min at room temperature, followed by a PBS. wash. Wells were then treated with Triton-X100 0.1% for 30 min at room temperature, and then blocked with 1% bovine serum albumin (Sigma) and stored at 4° C. until used.

The PCR products obtained were separated from free primers and unincorporated digoxigenin-dUTP using a Qiagen PCR purification kit according to the manufacturer's instructions. PCR products were eluted in a total volume of 100 $\mu$l 10 mM Tris-HCl, pH 9.0. Purified PCR samples were diluted 1:100 (1:25 in some cases when no ΨMTAP was visible on the gel) in BW buffer (6×SSC, 0.1% Tween-20), and 100 $\mu$l aliquots were added in triplicate to the streptavidin-coated plates, previously washed with PBS and BW buffer. After 1 h incubation at room temperature, wells were washed once with BW buffer and buffer B (800 mM NaCl, 100 mM Tris-HCl, pH 7.5, 0.5% Genius™ blocking reagent (Boehringer Mannheim), 5 mM maleic acid). Anti-digoxigenin antibody conjugated with horse radish peroxidase (150 U/ml, Boehringer-Mannheim) was diluted 1:1000 in buffer B and 100 $\mu$l aliquots were added to the wells and incubated for 30 min at 37° C. Plates were then washed once with buffer B and twice with buffer A (100 mM Tris-HCl, pH 7.5, 800 mM NaCl). To develop the ELISA, 100 $\mu$l of substrate solution (equal parts TMB and H202) were added to each well, followed by a 5 min incubation at room temperature. The reaction was stopped by addition of 100 $\mu$l of iM o-phosphoric acid. Plates were read in a microtiter plate spectrophotometer at a wavelength of 450 nm.

Gene Dosage Quantification. A regression line for each target sequence was calculated according to the standard curve data obtained in the ELISA from normal placenta DNA. The quotient of MTAP or p16 PCR product absorbance values (OD) divided by that of the ΨMTAP reference gene, derived from the standard curve for control DNA, was used to normalize the values. The tumor sample gene dosage ratio was calculated from the equation (example):

Sample MTAP gene dosage ratio=sample OD MTAP/sample OD ΨMTAP/control OD MTAP/control OD ΨMTAP PCR for each sample was done at least twice. Inter-assay coefficient of variation of the OD was <15%. A standard curve and calculation of the normalization factor from control DNA was done with each PCR assay. Only sample OD values in the linear range of the standard curves were considered for calculation. A sample was considered to have homozygous MTAP or p16 deletion when the normalized gene dosage ratio was <0.3. This criterion was chosen prior to the initiation of sample analysis based on previous reports utilizing differential PCR to detect p16 homozygous deletions.

Frequency of Homozygous Deletions of p16 and MTAP. Homozygous p16 deletions occurred in 25 out of 95 samples (26%), while homozygous MTAP deletions were observed in 22 out of 95 cases (23%) (Table 2). Fourteen samples (15%) had a co-deletion of both genes, 11 (12%) had only a p16 deletion, and 8 (8%) had only MTAP deletions (FIG. 1, Table 2).

TABLE 2

Incidence of Homozygous MTAP/p16 Deletions in Primary Brain Tumor Samples

| | | GENE MARKER | | | |
|---|---|---|---|---|---|
| | | MTAP+ | MTAP+/P16− | MTAP−/P16+ | MTAP−/P16− |
| TOTAL # PATIENTS: | 95 | 62/95 (65%) | 11/95 (12%) | 8/95 (8%) | 14/95 (15%) |
| HISTOLOGICAL SUBTYPES: | TOTAL | % | % | % | % |
| Low-grade Astrocytoma | 9 | 7/9 (78%) | 0/9 (0%) | 2/9 (22%) | 0/9 (0%) |
| Anaplastic Astrocytoma | 5 | 3/5 (60%) | 0/5 (0%) | 1/5 (20%) | 1/5 (20%) |
| Oligodendrogliomas | 14 | 12/14 (86%) | 0/14 (0%) | 1/14 (7%) | 1/14 (7%) |
| Oligoastrocytomas | 7 | 4/7 (57%) | 0/7 (0%) | 3/7 (43%) | 0/7 (0%) |
| Glioblastomas | 60 | 36/60 (60%) | 11/60 (18%) | 1/60 (2%) | 12/60 (20%) |

Relation to Grade. Classification of the tumor samples, with regard to histological type and grade, showed that homozygous p16 deletions were found predominantly in grade IV glioblastomas (23 out of 60, 38%; $p<0.0001$). Furthermore, the frequency of p16 deletions was higher in astrocytic tumors (32%) compared to oligodendrogliocytic tumors (7%), and was not found in mixed, oligo-astrocytomas (Table 2). Homozygous MTAP deletions could be detected in all histological types, but co-deletions with p16 were confined to high-grade glioblastomas (55% of all MTAP deletions). Homozygous MTAP deletions without p16 deletions were characteristics of lower grade-brain tumors ($p=0.0005$), with no obvious predominance of a distinct histological subgroup. Only one glioblastoma showed an MTAP-p 16+ configuration, and in this sample the values for the MTAP/$\Psi$MTAP ratio (0.28) and the p16/$\Psi$MTAP ratio (0.43) were very close to the 0.3 cut-off value. These results indicate that a homozygous MTAP deletion without a p16 deletion is associated with low-grade malignant gliomas.

Sixteen brain tumor xenografts were studied with the same primer sets (FIG. 3). Breakpoints between MTAP exons 4/5 and 7/8 were also found in the xenografts, as was the breakpoint between p15 and p16. None of the childhood tumors showed a MTAP deletion, whereas most of the adult tumors showed a partial or complete deletion of the MTAP gene. Furthermore, p16 was deleted in all but one of the adult tumors, but only in a single childhood tumor (FIG. 3). An inverse relation between p15 and p16 could be observed in these childhood gliomas. These results suggest that the isolated deletion of p15 is characteristic of childhood gliomas, whereas p16 and MTAP deletions distinguish adult gliomas.

EXAMPLE III

Fine Mapping of 9p21 Derangements in Brain Tumors

Fine Mapping. Fine mapping of the region between p15 and MTAP was performed in 37 primary tumors and in 16 xenografts using primers for recently identified sequence tagged sites (STS) as well as for the distinct exons of p15, p16, and MTAP (Table 1). The PCR was performed as described above; the gels were scanned and analyzed. Results were normalized according to the standard curves and gene dosage ratios compared to the $\Psi$MTAP values were calculated. A homozygous deletion was postulated, when the normalized gene dosage ratio was <0.3. In some borderline cases, an additional ELISA was performed.

Figure 2:
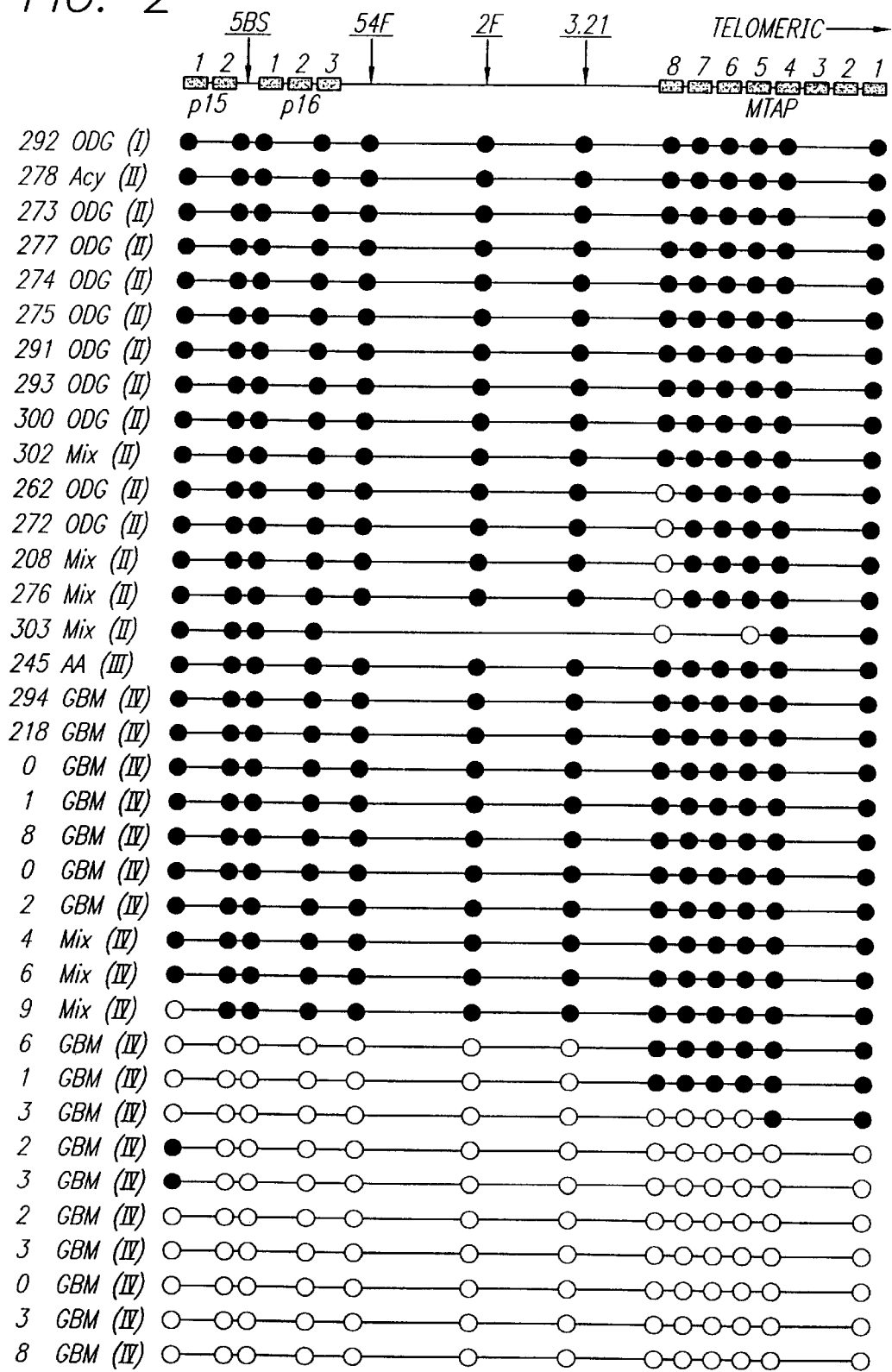
FIG. 2 is a graphic table which identifies the location of the earliest detectable homozygous deletions of a region of chromosome 9p21 in histological grade human primary tumor cell samples obtained as described in the Detailed Description. The identity of the tumor cell type and its histological grade is shown in the leftmost column of the table. Solid circles (•) in the remaining columns denote the absence of a deletion in the indicated region of 9p21 (normal gene structure) while an open circle (○) denotes a deletion in the region.

To investigate the locations of the different deletions, we performed fine mapping of the region between p15 and MTAP in 36 brain tumor samples. Recurrent breakpoints within the MTAP gene were detected between exons 4/5 (2 cases) and between exons 7/8 (4 cases). Histologic grade I–III tumors had much smaller deletions than grade IV (FIG. 2). The minimally deleted region encompassed the 3'-region of MTAP, with the breakpoints mentioned above. Homozygous deletion of MTAP in high-grade glioblastomas included the p16 gene in 10 out of 11 cases (FIG. 2). Only in one sample (#799) did the deletion start centromeric of p16, and involved the p15 gene. Two tumor samples showed a centromeric breakpoint between p15 and p16, and a telomeric breakpoint beyond MTAP (#802 and #803). In addition, breakpoints between MTAP exons 4/5 (#T303, #723) and between STS 3.21 and MTAP exon 8 (#756, #801) could be identified in samples from patients with glioblastomas (FIG. 2). This suggests the existence of fragile sites between STS 3.21 and MTAP exon 8, between MTAP exons 7 and 8, and between MTAP exons 4 and 5.

EXAMPLE IV

Measurement of Protein Expression from Deranged 9p21 Genes

Western Blot Analysis. Xenograft tumors were dissected using a razor blade. The sections were crushed in microfuge tubes containing 500 $\mu$l of RIPA-M buffer (50 mM NaCl, 50 mM Tris pH 7.4,: 0.5% NP-40, 1 mM EGTA, 1 nM Na3VO4, 1 mM NaF, 1 mg/ml aprotinin, 1 mg/ml leupeptin, 1 mM PMSF). Samples were further disrupted by passing several times through an 18G needle, then a 22G needle, a 27G, and incubated at 4° C. overnight. Then, samples were spun down at 12000 g for 10 min., and the protein in the supernatant was quantified with a Pierce Coomassie Plus™ Protein Assay Reagent (Rockford, Ill.). After boiling in sample buffer for 5 min., equal amounts of 50 $\mu$g were loaded onto 14% Tris-glycine gels (Novex, San Diego, Calif.), separated at 125V for 90 min, and transferred to PVDF-membranes (Millipore, Bedford, Mass.). Membranes were blocked overnight with 1% casein-blocking solution, and probed for 1 h at 20° C. with either a monoclonal mouse-anti-human p16-antibody (Pharmingen, San Diego, Calif.), or a polyclonal chicken antibody generated against recombinant human MTAP. Bound antibody was detected using Western-Light chemiluminescence detection kit (Tropix, Bedford, Mass.).

Reverse Transcriptase-PCR (RT-PCR). Total RNA was extracted from tumor tissues with a Qiagen™ kit. About 25 mg of tissue were homogenized by aspirating several times with a 1 cc syringe through a 22G needle in lysis buffer. RNA was eluted from spin columns in 30 $\mu$l DEPC-treated water. One $\mu$g of RNA was transcribed into single-stranded cDNA using a first-strand cDNA synthesis kit (Gibco-BRL, Gaithersburg, Md.), and random primers.

Figure 4:
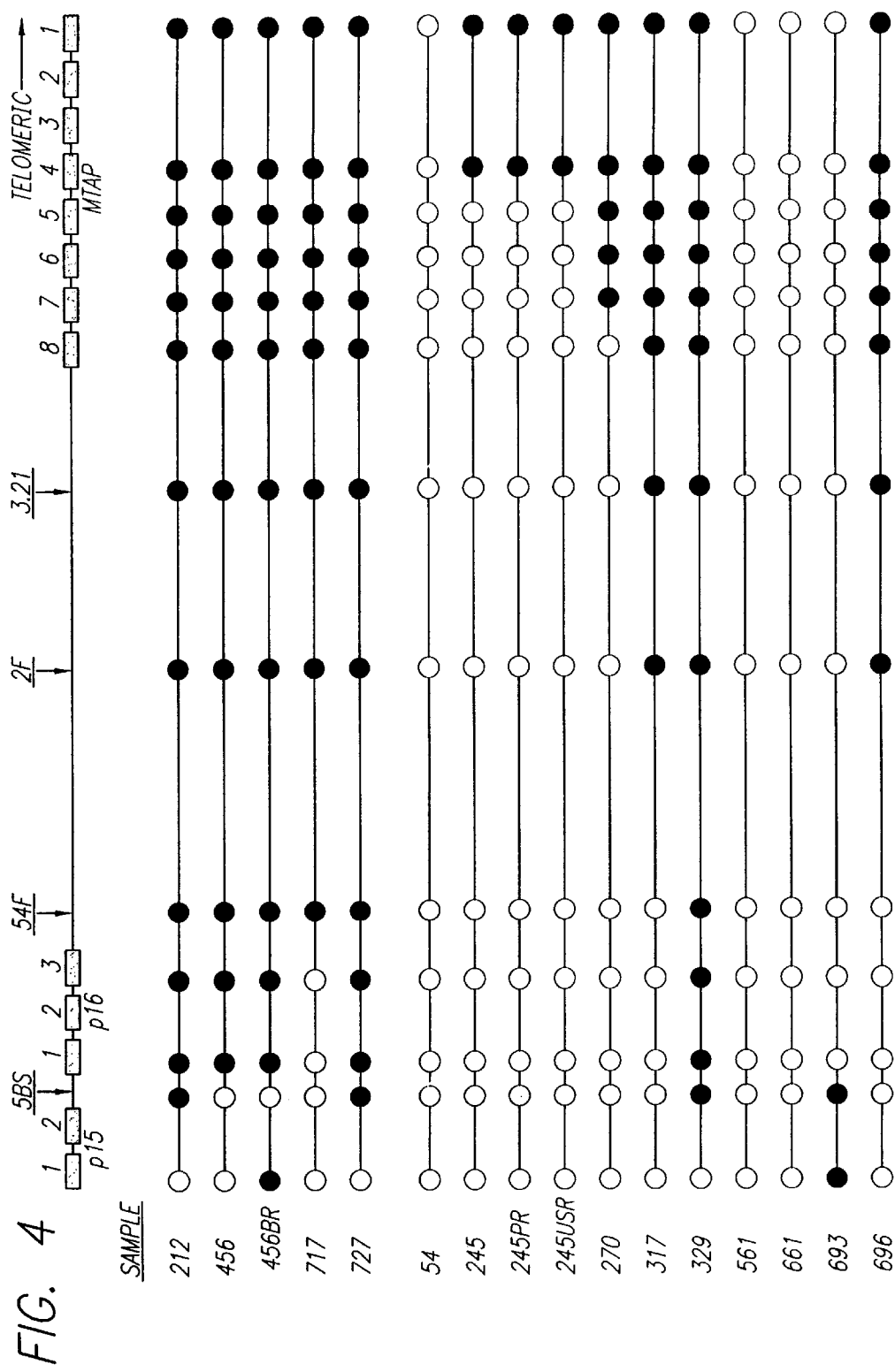
FIG. 4 is a graphic table which identifies the location of the earliest detectable homozygous deletions of a region of chromosome 9p21 in xenograft tumor cell samples obtained as described in the Detailed Description. The identity of the tumor tissue type is shown in the leftmost column of the table. Solid circles (●) in the remaining columns denote the absence of a deletion in the indicated region of 9p21 (normal gene structure) while an open circle (○) denotes a deletion in the region. The xenograft samples involving adult tumors are the 11 samples listed in the bottom half of the leftmost column, while samples involving childhood tumors are the 5 samples listed in the upper half of the leftmost column.

RT-PCR was carried out in a total volume of 25 $\mu$l including 3 $\mu$l cDNA 2.0 mM MgCl2, 200 $\mu$M dNTPs (Sigma, St. Louis, Mo.), 7.5 $\mu$mol of each primer, and 5 U AmpliTaq Gold™ DNA Polymerase (Perkin Elmer, Branchburg, N.J.) in the reaction buffer provided by the supplier. PCR conditions were as follows: Initial 5 min 94° C., 35 cycles of 94°, 30 sec., 58° C., 30 sec., 72°, 1 min., and a final extension of 7 min. at 72° C. Primers for GAPDH served as positive control (Table 1). PCR products were electrophoresed on a 2% agarose gel as indicated above. Chi-square test was used to determine statistical significance.

p16 and MTAP Protein Expression in Xenograft Tumors. Two out of 4 samples with an intact p16 gene did not express the p16 protein (FIG. 4a). This result is in accordance with previous findings that p16 is highly regulated in most human tumors and that homozygous deletion is not the only mechanism of inactivation. On the other hand, MTAP protein was found in all samples with an intact gene (FIG. 4b). Furthermore, two tumors (#245 and #270) with deletions of MTAP exons 5–8 and MTAP exon 8, respectively, produced immunoreactive MTAP proteins. The 32 kDa immunoreactive band in the tumor with an isolated exon 8 deletion was indistinguishable from the wild type MTAP protein.

EXAMPLE V mRNA MTAP Expression Analysis to Confirm Effect of Deletion

MTAP mRNA Expression in Xenografts. Because the antisense primer for the amplification of MTAP exon 8 is 225 bp downstream of the coding sequence, it was possible that the deletion in sample #270 is out of the coding sequence in the 3'-untranslated region. This could result in the synthesis of a normal molecular weight MTAP protein. We therefore performed RT-PCR with two different primer pairs. MTAP1×4 includes exactly the coding sequence from MTAP exon 1 to MTAP exon 4 (bases 122–468 according to the GeneBank mRNA sequence U22233), whereas MTAP5×8 amplifies exactly the region from the beginning of MTAP exon 5 to the end of the coding sequence in MTAP exon 8 (bases 469–973). We could amplify PCR-products with primers MTAP1×4 in both sample #245 and sample #270, but amplification with MTAP5×8 primers did not result in a PCR-product in either tumor (FIG. 5). Sample #696 served as a positive control. These results confirm the MTAP deletion and western blotting data, and suggest the existence of truncated forms of MTAP in some gliomas.

EXAMPLE VI

Analysis of NSCLC Tumor Samples

Tumor samples from 50 randomly selected male human patients were obtained, then prepared for analysis and analyzed as described in preceding Examples.

Guided by microscopic examination of representative slides, the DNA samples extracted from NSCLC specimens contained (30% contaminating normal tissue DNA. Homozygous MTAP deletions were detected in 19 of the 50 samples (38%) from patients with NSCLC (Table 3). Adenocarcinomas showed a higher frequency of homozygous deletions (11 of 25, 44%) than squamous cell carcinomas (6 of 21, 29%). Two of 4 large cell carcinoma samples were MTAP-deleted. No correlation between homozygous deletions and the age of the patients was evident.

In contrast to the results for MTAP, homozygous deletions of p16 exon 1a_ occurred in only 9 of 50 NSCLC samples (18%), including 4 of 25 adenocarcinomas (16%), 4 of 21 squamous cell carcinomas (19%) and 1 of 4 large cell carcinomas (Table 3). No patient had a p16 exon 1a$\alpha$ deletion without a deletion of MTAP exon 8, but 10 samples had homozygous. MTAP deletions without deletions of p16 exon 1 (the exon closest to MTAP).

TABLE 3

Incidence of Homzygous MTAP/p16 Deletions in NSCLC

| MTAP Deletions: | |
|---|---|
| Total | 19/50 (38%) |
| Adenocarcinoma | 11/25 (44%) |
| Squamous cell carcinoma | 6/21 (29%) |
| Large cell carcinoma | 2/4 (25%) |
| p16 Deletions (exons 1a$\alpha$, 3): | |
| Total | 9/50 (50%) |
| Adenocarcinoma | 4/25 (16%) |
| Squamous cell carcinoma | 4/21 (19%) |
| Large cell carcinoma | 1/4 (25%) |

Several samples had a p16/$\Psi$MTAP ratio of >1.25. These tumors may have had increased ploidy of chomosome 9, with or without a breakpoint between p16 and MTAP. On chromosome 9p21, p16 and MTAP lie in tail-to-tail orientation at a distance of approximately 100 kb. Because exon 3 of p16 lies closer (i.e. more telomeric) than exon 1 to MTAP exon 8, p16 exon 3 was amplified with specific primers in the 10 samples with deleted MTAP but intact p16 exon 1. None of these samples had a deletion of the p16 exon 3 region that encompasses the coding sequence.

To identify the smallest deleted region in the NSCLC samples with p16+/MTAP-status, a fine mapping analysis by quantitative PCR was performed according to the protocol described above. Consistent with findings in brain tumors described in the preceding examples, a frequent telomeric breakpoint was found within the MTAP gene between MTAP exon 4 and 5.

The invention having been fully described, modifications and extensions thereof may become obvious to those of ordinary skill in the art. All such modifications and extensions are within the scope of the invention.

Summary of Sequences

SEQ.ID.No.: 1 is a primer utilizable in the method of the invention.
SEQ.ID.No.: 2 is a primer utilizable in the method of the invention.
SEQ.ID.No.: 3 is a primer utilizable in the method of the invention.
SEQ.ID.No.: 4 is a primer utilizable in the method of the invention.
SEQ.ID.No.: 5 is a primer utilizable in the method of the invention.
SEQ.ID.No.: 6 is a primer utilizable in the method of the invention.
SEQ.ID.No.: 7 is a primer utilizable in the method of the invention.
SEQ.ID.No.: 8 is a primer utilizable in the method of the invention.
SEQ.ID.No.: 9 is a primer utilizable in the method of the invention.
SEQ.ID.No.: 10 is a primer utilizable in the method of the invention.
SEQ.ID.No.: 11 is a primer utilizable in the method of the invention.
SEQ.ID.No.: 12 is a primer utilizable in the method of the invention.

SEQ.ID.No.: 13 is a primer utilizable in the method of the invention.
SEQ.ID.No.: 14 is a primer utilizable in the method of the invention.
SEQ.ID.No.: 15 is a primer utilizable in the method of the invention.
SEQ.ID.No.: 16 is a primer utilizable in the method of the invention.
SEQ.ID.No.: 17 is a primer utilizable in the method of the invention.
SEQ.ID.No.: 18 is a primer utilizable in the method of the invention.
SEQ.ID.No.: 19 is a primer utilizable in the method of the invention.
SEQ.ID.No.: 20 is a primer utilizable in the method of the invention.
SEQ.ID.No.: 21 is a primer utilizable in the method of the invention.
SEQ.ID.No.: 22 is a primer utilizable in the method of the invention.
SEQ.ID.No.: 23 is a primer utilizable in the method of the invention.
SEQ.ID.No.: 24 is a primer utilizable in the method of the invention.
SEQ.ID.No.: 26 is a genomic sequence for the gene encoding methylthioadenosine phosphorylase.

What is claimed is:

1. A method for diagnosis or prognosis for cancer associated with deletions of chromosome 9p21, the method comprising:

(a) determining whether any portion of the 9p21 chromosome including and telomeric to sequence tagged site 3.21 is deleted; and, (b) determining whether any portion of the 9p21 chromosome centromeric to sequence tagged site 3.21 is deleted;

wherein a positive finding in step (a) and a negative finding in step (b) are indicative of a cancer at an early stage and, wherein a positive finding in step (a) and a positive finding in step (b) are indicative of a cancer at an advanced stage, thereby determining a diagnosis or prognosis for cancer.

2. The method according to claim 1, further comprising the use in step (a) of primer pairs selected from the group of oligonucleotides consisting of SEQ ID NOS:3 and 4, SEQ ID NOS:21 and 22 and SEQ ID NOS:23 and 24.

3. The method according to claim 1, further comprising the use in step (b) of primer pairs selected from the group of oligonucleotides consisting of SEQ ID NOS:5 and 6, SEQ ID NOS:7 and 8, SEQ ID NOS:9 and 10, SEQ ID NOS: 11 and 12, SEQ ID NOS:13 and 14, SEQ ID NOS:15 and 16 and SEQ ID NOS:17 and 18.

4. The method according to claim 1, further comprising the use of the primer pair of SEQ ID NOS:1 and 2 as a control for step (a).

5. The method according to claim 1, wherein the cancer is a glioma.

6. The method according to claim 1, wherein the cancer is a primary lymphoid malignancy.

7. The method according to claim 1, wherein the cancer is non-small cell lung cancer.

8. The method according to claim 1, wherein the cancer is a melanoma.

9. A method for diagnosis or prognosis for cancer associated with deletions of chromosome 9p21, the method comprising:
(a) determining whether any portion of the gene encoding metabolic enzyme mehylthioadenosine phosphphorylase is deleted; and,
(b) determining whether any portion of the 9p21 chromosome centromeric to sequence tagged site 3.21 is deleted;
wherein a positive finding in step (a) and a negative finding in step (b) are indicative of a cancer at an early stage and, wherein a positive finding in step (a) and a positive finding in step (b) are indicative of a cancer at an advanced stage, thereby determining a diagnosis or prognosis for cancer.

10. The method according to claim 9 wherein step (a) comprises determining whether exon 8 of the gene coding for metabolic enzyme mehylthioadenosine phosphphorylase is deleted.

11. The method according to claim 9 wherein step (a) comprises determining whether the region from exon 4 to exon 5 of the gene coding for metabolic enzyme mehylthioadenosine phosphphorylase is deleted.

12. The method according to claim 9 wherein step (b) comprises determining whether any portion of the gene coding for p16INK4A is deleted.

13. The method according to claim 9, further comprising the use in step (a) of primer pairs selected from the group of oligonucleotides consisting of SEQ ID NOS:3 and 4, SEQ ID NOS:21 and 22 and SEQ ID NOS:23 and 24.

14. The method according to claim 9, further comprising the use in step (b) of primer pairs selected from the group of oligonucleotides consisting of SEQ ID NOS:5 and 6, SEQ ID NOS:7 and 8, SEQ ID NOS:9 and 10, SEQ ID NOS:11 and 12, SEQ ID NOS:13 and 14, SEQ ID NOS:15 and 16 and SEQ ID NOS:17 and 18.

15. The method according to claim 9, further comprising the use of the primer pair of SEQ ID NOS:1 and 2 as a control for step (a).

16. The method according to claim 9, wherein the cancer is a glioma.

17. The method according to claim 9, wherein the cancer is a primary lymphoid malignancy.

18. The method according to claim 9, wherein the cancer is non-small cell lung cancer.

19. The method according to claim 9, wherein the cancer is a melanoma.

20. A method for diagnosis of, and determining a prognosis for, cancer causatively associated with derangements of chromosome 9p21, the method comprising:
(a) determining whether any portion of the gene encoding metabolic enzyme mehylthioadenosine phosphphorylase is deleted; and,
(b) determining whether any portion of the gene coding for p16INK4A is deleted;
wherein a positive finding in step (a) and a negative finding in step (b) are indicative of a cancer at an early stage and, wherein a positive finding in step (a) and a positive finding in step (b) are indicative of a cancer at an advanced stage, thereby determining a diagnosis or prognosis for cancer.

21. The method according to claim 20, further comprising the use in step (a) of primer pairs selected from the group of oligonucleotides consisting of SEQ ID NOS:3 and 4, SEQ ID NOS:21 and 22 and SEQ ID NOS:23 and 24.

22. The method according to claim 20 further comprising the use in step (b) of primer pairs selected from the group of oligonucleotides consisting of SEQ ID NOS:5 and 6, SEQ ID NOS:7 and 8, SEQ ID NOS:9 and 10, SEQ ID NOS:11 and 12, SEQ ID NOS:13 and 14, SEQ ID NOS:15 and 16 and SEQ ID NOS:17 and 18.

23. The method according to claim 20, further comprising the use of the primer pair of SEQ ID NOS:1 and 2 as a control for step (a).

24. The method according to claim 20, wherein the cancer is a glioma.

25. The method according to claim 20, wherein the cancer is a primary lymphoid malignancy.

26. The method according to claim 20, wherein the cancer is non-small cell lung cancer.

27. The method according to claim 20, wherein the cancer is a melanoma.

* * * * *